United States Patent [19]

Zagame

[11] Patent Number: 5,613,893
[45] Date of Patent: Mar. 25, 1997

[54] DORSO-ABDOMINAL SUPPORT GARMENT

[76] Inventor: André Zagame, 55 rue de l'Eglise, 61110 Remalard, France

[21] Appl. No.: 233,953

[22] Filed: Apr. 28, 1994

[30] Foreign Application Priority Data

May 4, 1993 [FR] France ................................ 93 05286

[51] Int. Cl.$^6$ ........................................................ A41C 1/08
[52] U.S. Cl. ............................... 450/155; 450/132; 2/73; 2/406; 2/311
[58] Field of Search ............................. 2/44, 73, 92, 79, 2/69, 69.5, 227, 400, 401, 402, 403, 406, 338, 310, 311, 312; 450/155, 132, 115, 116, 117, 118, 119, 120, 121, 122, 123, 124, 125, 126, 127, 128, 129, 130, 131; 602/19

[56] References Cited

U.S. PATENT DOCUMENTS

| | | |
|---|---|---|
| D. 218,586 | 9/1970 | Williams .......................... 450/155 X |
| 571,172 | 11/1896 | Provoost .......................... 450/155 |
| 1,185,672 | 6/1916 | Hueltner .......................... 450/155 X |
| 1,276,410 | 8/1918 | Pratt .......................... 450/155 |
| 1,661,720 | 3/1928 | Fontaine . | 
| 2,584,279 | 2/1952 | McDowell . |
| 2,586,658 | 2/1952 | Hormann . |
| 2,765,470 | 10/1956 | Read . |
| 2,896,634 | 7/1959 | Beder .......................... 450/155 X |
| 2,955,598 | 10/1960 | Blatt .......................... 450/155 X |
| 3,080,869 | 3/1963 | Alberts .......................... 450/155 X |
| 4,557,268 | 12/1985 | Maddux et al. .......................... 450/155 |
| 4,697,592 | 10/1987 | Maddux et al. .......................... 450/155 |

FOREIGN PATENT DOCUMENTS

| | | |
|---|---|---|
| 487766 | 12/1918 | France . |
| 617964 | 11/1926 | France . |
| 1213302 | 10/1959 | France . |

*Primary Examiner*—Jeanette E. Chapman
*Attorney, Agent, or Firm*—Sixbey, Friedman, Leedom & Ferguson, P.C.; Gerald J. Ferguson, Jr.; Tim L. Brackett, Jr.

[57] ABSTRACT

A dorso-abdominal support belt constituted by unitary assembly having a crotch piece, and organized to exert permanent compression on the zone concerned of the body. According to the invention, the unitary assembly comprises two complementary portions connected together by an associated seam, said portions comprising an enveloping front-and-back main portion made of a first elastic textile material selected to exert controlled support, and an abdominal portion made of a second elastic textile material which is substantially more stretchable than said first material, such that said abdominal portion allows freer swelling of the abdomen, and wherein a peripheral band is associated with the unitary assembly, being connected to said assembly via seams that are disposed so that the peripheral band can exert additional support in the super-pubic and/or pre-umbilical zone.

8 Claims, 1 Drawing Sheet

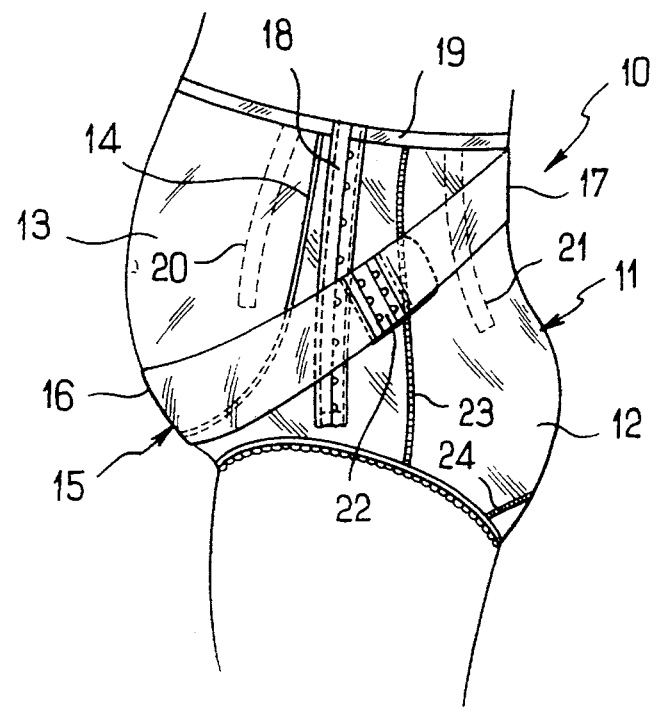
FIG_1
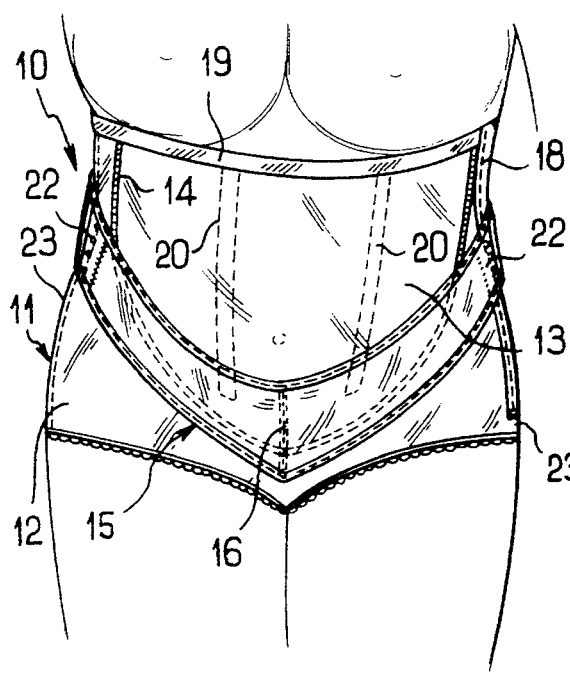
FIG_2
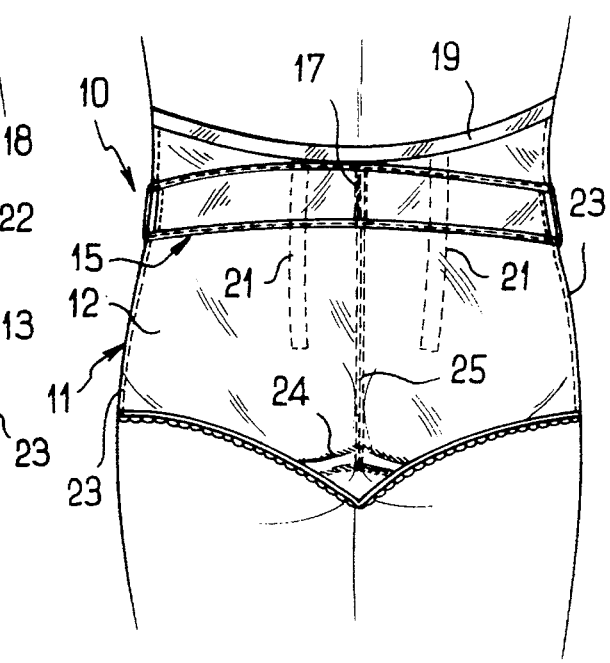
FIG_3

DORSO-ABDOMINAL SUPPORT GARMENT

The present invention relates to dorso-abdominal support belts which are constituted by a unitary assembly having a crotch piece and organized to exert permanent compression on the zone of the body that is concerned.

BACKGROUND OF THE INVENTION

In the context of the invention, the term "belt" must be understood in a wide sense, i.e. it covers low girdles, high girdles, and various types of brace that extend downwards (even to below the knees) and/or upwards (possibly having two shoulder straps).

Such belts are commonly used to eliminate or at least reduce marks or scars forming folds of fibrous tissue that remain after treatment of deep lesions of the skin. They are recommended in particular by specialists of the following kinds of surgery: obstetric, digestive or visceral, and plastic or reconstructive.

Conventional support belts are made in the form of a unitary assembly of elastic textile material specially designed to exert permanent compression that is as controlled as possible on the zone concerned of the body, and in particular on the dorso-abdominal zone. Certain more elaborate belts specially selected for post-operative conditions comprise a crotch piece provided with a hook fastening having the effect that tension tends to be exerted both horizontally and vertically. A unitary assembly is thus obtained which is both effective as to its anti-edematal therapeutic effect, and attractive in appearance for the person wearing the support belt.

However, in certain situations, such belts are poorly or badly adapted to being worn for an extended period. This applies in particular to pregnant women insofar as the swelling of the abdomen interferes with the distribution of tension within the elastic cloth.

If a dorso-abdominal belt is fitted to exert controlled support at the beginning of pregnancy, then the swelling of the abdomen has the effect of giving rise locally to a support pressure that considerably exceeds 25 mmHg, with the risk of interfering with muscular functions and with a loss of control over the support exerted. However, if the belt is fitted to take account of future swelling of the abdominal, then the support exerted at the beginning of pregnancy will generally be insufficient, and in addition subsequent control of the support exerted will become more and more unpredictable as pregnancy advances. Under such circumstances, there is an even more frequent risk of encountering syndromes of the Lacome syndrome type (osteo-ligamento-muscular syndrome), with the appearance of fatigue and/or pain, and the woman feels a pressing need for relief that the belt cannot provide her.

The present invention seeks, in particular, to solve that problem by designing a dorso-abdominal support belt that does not have the above-mentioned drawbacks and limitations.

The person skilled in the art might be tempted to seek inspiration from comfort belts that already exist for satisfying the special case of pregnant women. However such belts are designed exclusively as comfort belts: in general single or double lacing extending in the vertical direction is used to vary the total abdominal circumference, and that goes directly against the looked-for therapeutic action of controlled support (on the contrary, rigid lacing runs the risk of interfering with muscular functions because of excessive compression), not to mention the material used which is of greater or lesser thickness and is not designed to exert permanent compression on the zone concerned of the body.

As a result, articles that already exist in specialized underwear for pregnant women is of no help in solving the above-mentioned problem relating to applying controlled support.

To round off the state of the art, mention may also be made of some very old solutions, the wearing of which would nowadays be prohibited because of their inability to control the support applied, which support is indeed nearly always circular only, thus running a risk of interfering with muscular functions.

Document U.S. Pat. No. 2,586,658 thus describes a back brace constituted by a back portion made of inelastic material and a front portion made of elastic cloth, having shoulder straps that are attached to a pubic gusset sewn onto said front portion. Because there is no crotch piece the support exerted by such a brace is circular only, and above all it cannot be controlled because of the inelastic nature of the back portion. In addition, the straps of that brace go against anatomy because the back fastenings are placed very high relative to the L4 and L5 lumbar vertebrae. Finally, such a design is quite unsuitable for a pregnant woman since the fastening of the straps on the pubic gusset constitutes rigid strapping passing over the abdomen which would constitute a danger for the pregnant woman.

Document FR-E-20 728 describes a pregnancy belt which is merely an abdominal support strap having elastic tapes serving to relieve the abdominal in the pubic region. Such a strap cannot perform genuine therapeutic support. In addition, the presence of fixing loops of non-elastic cloth makes it impossible to provide any control over the pressure exerted by the elastic tapes.

Document FR-A-617 964 describes a pregnancy garment made of ribbed cloth having inextensible front-and-back flat tapes stitched thereon together with oblique flat straps of extra-strong elastic cloth. Such a garment can exert circular support only and it does so with the risk of interfering with the large muscles. The inextensible tapes are particularly inappropriate for free play of muscular functions (and indeed, even in the event of muscular deficiency, interference with muscular functions gives rise to atrophy of said functions).

The technological background may be illustrated by referring to the following documents: U.S. Pat. No. 2,765,470, FR-A-1 213 302, U.S. Pat. No. 1,661,720, and U.S. Pat. No. 2,584,279.

OBJECTS AND SUMMARY OF THE INVENTION

An object of the present invention is thus to provide a dorso-abdominal belt capable of accepting a certain amount of increase in the volume of the patient while maintaining control over the support exerted in a manner that is uniform and multidirectional, and doing so without risk of excessive compression, even locally, for the person wearing the belt.

More particularly, the present invention provides a dorso-abdominal support belt constituted by unitary assembly having a crotch piece, and organized to exert permanent compression on the zone concerned of the body, wherein the unitary assembly comprises two complementary portions connected together by an associated seam, said portions comprising an enveloping front-and-back main portion made of a first elastic textile material selected to exert controlled support, and an abdominal portion made of a second elastic textile material which is substantially more stretchable than said first material, such that said abdominal portion allows freer swelling of the abdomen, and wherein a peripheral band is associated with the unitary assembly, being connected to said assembly via seams that are disposed so that the peripheral band can exert additional support in the super-pubic and/or pre-umbilical zone.

Preferably, the abdominal portion of the unitary assembly is connected to the main portion of said assembly via a U-shaped seam whose curved portion is essentially covered by the front portion of the peripheral band.

Also advantageously, the unitary assembly includes on one side a hook-fastened placket for making said belt easier to put on. In particular, the hook fastening includes a plurality of rows of hooks so as to enable the circumferential size of said belt to be adjusted.

It may also be advantageous for the unitary assembly to be reinforced by stiffening in order to obtain better support, preferably with two front stiffeners and two back stiffeners.

Also preferably, the peripheral band is connected to the unitary assembly via seams relating to the front middle zone and/or to the back middle zone of said band, the remainder of the band resting freely against the surface of said unitary assembly.

It is then advantageous for the seams connecting the peripheral band of the unitary assembly to form at least one front middle fixing line and at least one back middle fixing line, said two fixing lines being the only points of connection between said band and said unitary assembly. In particular, the front middle fixing line is disposed in the super-pubic zone of the unitary assembly and the back middle fixing line is disposed in the top back zone of said unitary assembly.

It is also advantageous for each side the peripheral band to have a gap provided with a plurality of rows of hooks, thereby enabling the circumferential size of said band to be adjusted.

Finally, it is advantageous for the peripheral band to be made of an elastic textile material, said material being preferably essentially identical to the first material constituting the unitary assembly.

BRIEF DESCRIPTION OF THE DRAWING

Other characteristics and advantages of the invention appear more clearly in the light of the following description and the accompanying drawing in which FIGS. 1 to 3 are respectively a side view, a front view, and a back view of a dorso-abdominal support belt of the invention, and in this case a belt of the low girdle type worn by a pregnant woman.

MORE DETAILED DESCRIPTION

FIGS. 1 to 3 show a dorso-abdominal support belt 10 of the invention which is constituted by a unitary assembly 11 organized to exert permanent compression on the zone concerned of the body, said assembly comprising a crotch piece (not visible in the figures) which is preferably fitted with a hook fastener that is preferably adjustable and that has the effect that tension tends to be exerted both horizontally and vertically.

According to a characteristic of the invention, the unitary assembly 11 is made up of two complementary portions 12 and 13 that are connected together by an associated seam 14, said portion comprising a main enveloping front-and-back portion 12 and an abdominal portion 13, said two portions being made of textile material having different elasticity characteristics. The enveloping front-and-back main portion 12 is made of a first elastic textile material selected to exert controlled two-directional support, whereas the abdominal portion 13 is made of a second elastic textile material that is considerably more extensible than the first material, so that said abdominal portion 13 allows greater freedom for swelling of the abdomen. Thus, as can be seen more clearly in FIG. 2, the abdominal portion 13 of the unitary assembly 11 is connected to the main portion 12 of said assembly via an outline 14, i.e. via the connecting seam, that is U-shaped, with the curved portion thereof being essentially overlaid by the front portion of a peripheral band 15 associated with the unitary assembly 11, which band is described in greater detail below both with respect to its structure and its function. The material from which the enveloping front-and-back main portion 12 is made is preferably an elastic textile material of the Lycra type as is conventionally used for existing support belts, in particular for the treatment of scar-hypertrophy in patients who have been severely burnt (when uniform control support is essential). Such a material makes it possible to exert controlled pressure, generally in the range 16 mmHg to 24 mmHg. In contrast, the abdominal portion 13 is made of a material that is more flexible, e.g. significantly stretchier Lycra that exerts support pressure that does not exceed 15 mmHg.

Such a structure comprising two complementary portions makes it possible both to control the support exerted and to allow the abdomen to swell progressively without giving rise to excessive compression in the abdominal zone of the person wearing the dorso-abdominal support belt. It then becomes possible for a given person to select a support belt having the right size at the beginning of pregnancy or during pregnancy without subsequent abdominal swelling running any risk of causing excessive compression because of the highly extensible nature of the abdominal portion of the unitary assembly.

In general, five or six different sizes need to be provided to be able to fit various sizes of pelvis properly. Controlled support requires a minimum of five or six different sizes in practice so as to make it possible to fit the belt with optimum effectiveness to different pelvis sizes and shapes. In certain extreme cases where the shape of a patient is not standard, it can be essential to have a belt made to measure for that patient.

According to another characteristic of the invention, a peripheral band 15 is associated with the unitary assembly 11, being connected to said assembly via seams which are disposed in such a manner that the peripheral band is capable of exerting additional support in the super-pubic and/or pre-umblical zone. As can be seen more clearly in FIG. 1, the peripheral band 15 is organized as an under-belly band combining the effect of abdominal support and the therapeutic effect of controlled pressure support.

The unitary assembly 11 is made in this case in the form of a short girdle, that is terminated at the top by an elastic waistband 19, but that is naturally merely an example. The various component parts of the enveloping front-and-back main portion 12 are connected together by two lateral seams 23 and a back seam 25 (visible in FIG. 3 only), possibly together with shorter additional seams such as the bottom seam 24 that runs into the above-mentioned back seam 25. However, the fundamental seam of the support belt of the invention is the above-mentioned U-shaped seam 14 that connects the abdominal portion 13 to the enveloping front-and-back main portion 12.

As can be seen more clearly in FIG. 1, it is advantageous to provide the unitary assembly 11 with a placket on one side having a hook fastening for the purpose of making it easier to put on the support belt. The hook fastening 18 is placed on the side which is an advantage with respect to interfering with muscular functions, by providing an essentially vertical placket in the enveloping front-and-back portion 12. It is preferable to provide two or three vertical rows of hooks so as to make it possible to provide finer circumferential adjustment.

In addition, as is conventional in the field of dorso-abdominal support belts, it may be advantageous to provide reinforcement in the unitary assembly 11 by means of stiffening to provide better support, preferably using two front stiffeners 20 and two back stiffeners 21, the stiffeners being held in associated inside stitching and being covered by an inside layer of soft cloth to make them more comfortable.

As mentioned above, and according to another characteristic of the invention, a peripheral band 15 is associated with the unitary assembly 11 by being connected to said assembly by seams which are organized in such a way as to enable the band to exert additional support in the super-pubic and/or pre-umbilical zone.

A connection could be provided by means of a single seam, however that would run the risk of making it possible for the band to move undesirable as a function of the movements of the person wearing the support belt, thereby hindering the therapeutic support action that it is desired to apply in a precise subabdominal zone. That is why, in this case, a connection is provided between the peripheral band 15 and the unitary assembly 11 via seams 16 and 17 relating to the front middle zone and/or to the back middle zone of the band, with the remainder of said band resting freely against the surface of said unitary assembly. Providing two seams 16 and 17 thus appears to be preferable to using one of those two seams only, which one seam could then be either the front middle zone or else the back middle zone of the peripheral band. It turns out that optimum therapeutic action is obtained by providing for the seams 16 and 17 to form at least one front middle fixing line and at least one back middle fixing line, with these two lines being the only point where the peripheral band 15 is connected to the unitary assembly 11. More precisely, the front middle fixing line 16 (visible in FIGS. 1 and 2) is disposed in the super-pubic zone of the unitary assembly 11, while the back middle fixing line 17 (visible in FIGS. 1 and 3) is disposed in the top back zone of said unitary assembly. That disposition makes it possible both to maintain proper orientation of the peripheral band 15, which special orientation is of the sub-belly band type as is clearly visible in FIG. 1, while also accurately controlling the forces exerted by this band which is slightly stretched so as to provide the additional support which is exerted by said band.

Naturally, the seams 16 and 17 could be replaced by two or more adjacent parallel seams, while nevertheless taking care to ensure that symmetry of the disposition is maintained firstly in the super-pubic zone of the unitary assembly and secondly in the top back zone of said unitary assembly.

In general, it is also advantageous to provide the possibility of adjusting the circumferential size of the peripheral band. One such possibility is shown herein: in FIGS. 1 and 2 it can be seen that the peripheral band 15 has, on either side, a gap having several lines of hooks 22, thereby enabling the circumferential size of said band to be adjusted. It is thus possible to provide a sequence of five or six parallel rows of hooks, thereby enabling the righthand portion and the lefthand portion of the peripheral band 15 to be adjusted finely and independently of each other. Because of predetermined positioning of the rows selected as a function of increase in the volume of the abdomen during pregnancy, quantified adjustments are made available enabling the woman to relax the tension exerted by the band most progressively, e.g. by using a new row of hooks each month starting from the 20th week of pregnancy. It would naturally be possible to replace the hooks by equivalent fastening means, e.g. by Velcro type fasteners.

To make the peripheral band 15, it is preferable to use an elastic textile material that is essentially identical to the material used for making the unitary assembly 11, e.g. a Lycra that is accurately designed to exert support with pressure lying in the range 17 mmHg to 21 mmHg.

As will easily be understood, the dorso-abdominal support belt 10 is easily put on after the hook fastener 18 has been opened, and possibly also after opening or loosening at least one line of hooks 22 in the peripheral band 15. Once the support belt is properly in place and at the right height, the above-mentioned fastenings are easily closed so as to obtain the desired therapeutic action with accurately controlled support over the entire zone of the body that is enclosed.

It has thus been possible to make a dorso-abdominal support belt capable of accommodating a certain amount of increase in the volume of the patient, in particular the abdominal swelling of a pregnant woman, while maintaining control over the support that is exerted, with this being done without risk of excessive compression, even locally, for the person wearing the belt.

The support belt of the invention is thus applicable in numerous therapeutic treatments, and, by way of example mention may be made of the following kinds of surgery: obstetric, digestive, visceral, plastic, and reconstructive; and also treatment of sciatica and lumbago.

The invention is not limited to the embodiment described above, but on the contrary covers any variant that uses equivalent means to reproduce the essential characteristics specified above.

I claim:

1. A dorso-abdominal support garment including a unitary assembly having a crotch piece, and organized to exert permanent compression on a concerned zone of the body, said unitary assembly comprising two complementary portions consisting of an enveloping front-and-back main portion made of a first elastic textile material selected to exert controlled support, and an abdominal portion made of a second elastic textile material which is substantially more stretchable than said first material, such that said abdominal portion allows a freer swelling of the abdomen, wherein an elastic peripheral band is connected to the unitary assembly, said peripheral band being made of an elastic textile material, and being connected to said assembly via seams relating to the front middle zone and to the back middle zone of said band, said seams forming one front middle fixing line and one back middle fixing line which are the only points of connection between said band and said unitary assembly, the remainder of said band resting freely against the surface of said unitary assembly so that said peripheral band can exert additional support in the super-pubic zone and the pre-umbilical zone.

2. A support garment according to claim 1, wherein the abdominal portion of the unitary assembly is connected to the main portion of said assembly via a U-shaped seam whose curved portion is essentially covered by the front portion of the peripheral band.

3. A support garment according to claim 1, wherein the unitary assembly includes on one side a hook-fastened placket for making said garment easier to put on.

4. A support garment according to claim 3, wherein the hook fastening includes a plurality of rows of hooks so as to enable the circumferential size of said garment to be adjusted.

5. A support garment according to claim 1, wherein the unitary assembly is reinforced by stiffening in order to obtain better support, preferably with two front stiffeners and two back stiffeners.

6. A support garment according to claim 1, wherein the front middle fixing line is disposed in the super-pubic zone of the unitary assembly and the back middle fixing line is disposed in the top back zone of said unitary assembly.

7. A support garment according to claim 1, wherein on each side the peripheral band has a gap provided with a plurality of rows of hooks, thereby enabling the circumferential size of said band to be adjusted.

8. A support garment according to claim 1, wherein the elastic textile material of said peripheral band is essentially identical to the first elastic textile material constituting the enveloping front-and-back main portion of the unitary assembly.

* * * * *